United States Patent [19]

Fischer, deceased et al.

[11] 4,077,797

[45] Mar. 7, 1978

[54] 1-POLYFLUOROALKOXYPHENYL-4-SUB-STITUTED-5-HALOPYRIDAZONES-6 AND HERBICIDAL USES THEREOF

[75] Inventors: Adolf Fischer, deceased, late of Mutterstadt, Germany, by Caecilia Emma Fischer, heiress-at-law; Hanspeter Hansen, Ludwigshafen; Wolfgang Rohr, Mannheim, both of Germany

[73] Assignee: BASF Aktiengesellschaft, Ludwigshafen (Rhine), Germany

[21] Appl. No.: 690,266

[22] Filed: May 26, 1976

[30] Foreign Application Priority Data

Jun. 14, 1975 Germany .............................. 2526643

[51] Int. Cl.$^2$ ................. C07D 237/22; C07D 237/16; A01N 9/22

[52] U.S. Cl. .................................. 71/92; 260/250 A; 260/250 AH

[58] Field of Search ........................ 260/250 A; 71/92

[56] References Cited

U.S. PATENT DOCUMENTS

| 3,644,355 | 2/1972 | Ebner et al. ..................... 260/250 A |
| 3,697,522 | 10/1972 | Reichender et al. ............ 260/250 A |

*Primary Examiner*—Donald G. Daus
*Assistant Examiner*—Mark L. Berch
*Attorney, Agent, or Firm*—Keil, Thompson & Shurtleff

[57] ABSTRACT

1-Polyfluoroalkoxyphenyl-4-substituted-5-halopyridazones-6 in which the 4-substituent is amino, monoalkylamino, dialkylamino (1 to 3 carbon atoms per alkyl) or lower alkoxy, chloroacetamido, $CH_3COOCH_2$—CO—NH— or trimethylenimino and herbicidal uses thereof to control growth of unwanted plants among crop plants, especially cotton.

5 Claims, No Drawings

1-POLYFLUOROALKOXYPHENYL-4-SUBSTITUTED-5-HALOPYRIDAZONES-6 AND HERBICIDAL USES THEREOF

The present invention relates to new and valuable substituted pyridazones, a process for the manufacture thereof, their use as herbicides, and herbicides containing these compounds.

It is known to use 1-phenyl-4-amino-5-chloro (or bromo)-pyridazone-6 (German 1,105,232), 1-(3-trifluoromethylphenyl)-4-methoxy-5-chloropyridazone-6 (German 1,670,315), 1-(3-trifluoromethylphenyl)-4-dimethylamino-5-chloropyridazone-6 or 1-(3-trifluoromethylphenyl)-4-methylamino-5-chloropyridazone-6 (Swiss 482,684) as herbicides. However, they cause damage to some crop plants, particularly cotton, or have only a weak herbicidal action.

We have now found that substituted pyridazones of the formula

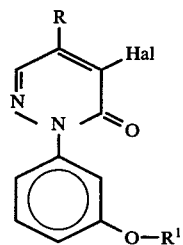

where Hal denotes halogen (chloro, bromo), $R^1$ denotes unsubstituted lower fluoroalkyl or lower fluoroalkyl substituted by chloro or bromo, and R denotes amino, alkylamino or dialkylamino having 1 to 3 carbon atoms per alkyl, the alkyl radicals being identical or different, R further denotes alkoxy of 1 to 3 carbon atoms, chloroacetamido, the radical $CH_3COOCH_2\text{-}CO\text{-}NH\text{-}$ or trimethylenimino, cause less damage to crop plants, especially cotton, than the prior art active ingredients, and have a better herbicidal action.

The new compounds are prepared by reacting a pyridazone derivative of the formula

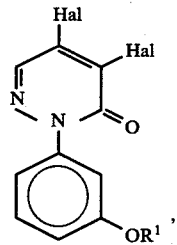

where Hal and $R^1$ have the above meanings, with ammonia; an alkylamine or dialkylamine of 1 to 3 carbon atoms per alkyl; trimethylamine; or an alcoholate of 1 to 3 carbon atoms, and the reaction product is if desired reacted with chloroacetyl chloride or acetylglycolic acid chloride.

The m-tetrafluoroethoxyphenylhydrazine required as precursor is obtained in conventional manner from the corresponding diazonium salt by reduction, and may be reacted, without isolation, with a 3-formyl-2,3-dihaloacrylic acid to give the corresponding pyridazone. A purer end product is, however, obtained when the m-tetrafluoroethoxyphenylhydrazine is isolated as the hydrochloride.

EXAMPLE 1

(a) 314 parts (by weight) of m-tetrafluoroethoxyaniline (W.A. Sheppard, J.Org.Chem., 29, 1, 1964) is diazotized with $NaNO_2$ and $H_2SO_4$; reduction to m-tetrafluoroethoxyphenylhydrazine is carried out with $Na_2SO_3$, and subsequently m-tetrafluoroethoxyphenylhydrazine hydrochloride is precipitated out with concentrated hydrochloric acid. The hydrochloride is suspended in 6 liters of 1N HCl, 228 parts of mucochloric acid is added and the mixture kept for 3 hours at 90° C. The 1-(m-tetrafluoroethoxyphenyl)-4,5-dichloropyridazone-6 which forms is suction filtered and recrystallized from cyclohexane.

Yield: 399 parts (74.5% of theory) Melting point: 74° to 75° C.

(b) A suspension of 18 parts (by weight) of 1-(m-tetrafluoroethoxyphenyl)-4,5-dichloropyridazone-6 in 100 parts of water and 50 parts of 40% (wt%) dimethylamine solution is heated for 30 minutes at 60° to 70° C. After the mixture has cooled, there is isolated 14 parts of 1-(m-tetrafluoroethoxyphenyl)-4-dimethylamino-5-chloropyridazone-6 having a melting point of 131° to 132° C (from cyclohexane).

(Active ingredient I)

EXAMPLE 2

10 parts of 1-(m-tetrafluoroethoxyphenyl)-4,5-dichloropyridazone-6 and 5 parts of 30% sodium methylate solution in methanol are refluxed for 10 minutes. After water has been added there is obtained 7 parts of 1-(m-tetrafluoroethoxyphenyl)-4-methoxy-5-chloropyridazone-6 having a melting point of 119° to 120° C (from cyclohexane/benzene).

(Active ingredient III)

EXAMPLE 3

A suspension of 10 parts of 1-(m-tetrafluoroethoxyphenyl)-4,5-dichloropyridazone-6 in 50 parts of water and 50 parts of 40% methylamine solution is stirred for 5 hours at 30° C. Suction filtration gives 9 parts of 1-(m-tetrafluoroethoxyphenyl)-4-methylamino-5-chloropyridazone-6 having a melting point of 188° to 189° C (from ethanol).

(Active ingredient IV)

The following compounds were prepared analogously;

1-(m-tetrafluoroethoxyphenyl)-4,5-dibromopyridazone-6(m.p.: 63° to 65° C) was also used as starting material:

1-(m-tetrafluoroethoxyphenyl)-4-amino-5-chloropyridazone-6 m.p. 173° to 174° C.

1-(m-tetrafluoroethoxyphenyl)-4-amino-5-bromopyridazone-6 m.p. 178° to 179° C.

1-(m-tetrafluoroethoxyphenyl)-4-methylamino-5-bromopyridazone-6 m.p. 177° to 178° C.

1-(m-tetrafluoroethoxyphenyl)-4-dimethylamino-5-bromopyridazone-6 m.p. 112° to 113° C.

1-(m-tetrafluoroethoxyphenyl)-4-methoxy-5-bromopyridazone-6 m.p. 107° to 108° C.

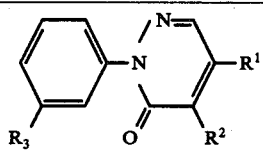

| R¹ | R² | R³ | M.p. (° C) |
|---|---|---|---|
| —N(H)(C(O)CH₂Cl) | Cl | —OCF₂—CHF₂ | 97 |
| —N(H)(C(O)CH₂—O—C(O)—CH₃) | Cl | —OCF₂—CHF₂ | 79 |
| —N(cyclopropyl) | Cl | —OCF₂—CHF₂ | 106–107 |
| —N(H)(H) | Cl | —OCHF₂ | 177–178 |
| —N(H)(CH₃) | Cl | —OCHF₂ | 162–163 |
| —N(CH₃)(CH₃) | Cl | —OCHF₂ | 69–70 |
| —N(H)(C(O)CH₂Cl) | Cl | —OCHF₂ | 124–125 |
| —N(H)(C(O)CH₂—O—C(O)—CH₃) | Cl | —OCHF₂ | 124–125 |
| —OCH₃ | Cl | —OCHF₂ | 161–162 |
| —N(CH₃)₂ | Cl | —OCF₂—CHF₂ | 126–127 |
| —O—CH₃ | Cl | —OCF₂—CHF₂ | 111–112 |
| —NH—CH₃ | Cl | —OCF₂—CHF₂ | 186–187 |
| —N(CH₃)₂ | Cl | —OCF₃ | 126–127 |
| —N(CH₃)₂ | Br | —OCF₃ | 136–137 |
| —OCH₃ | Br | —OCF₃ | 132–133 |
| —OCH₃ | Cl | —OCF₃ | 140–141 |
| —NHCH₃ | Cl | —OCF₃ | 143–144 |
| —NHCH₃ | Br | —OCF₃ | 137–138 |
| —NH₂ | Br | —OCF₃ | 172–173 |
| —OCH₃ | Br | —OCHF₂ | 143–144 |
| —NH₂ | Br | —OCHF₂ | 185–186 |
| —N(CH₃)₂ | Br | —OCHF₂ | 107–108 |
| —NHCH₃ | Br | —OCHF₂ | 156–157 |
| —NHCOCH₂Cl | Br | —OCHF₂ | 121–122 |
| —NH—CO—CH₂OCOCH₃ | Br | —OCHF₂ | 90–91 |
| —OCH₃ | Br | —OCF₂—CHFCl | 135–136 |
| —N(CH₃)₂ | Cl | —OCF₂—CHFCl | 103–104 |
| —N(CH₃)₂ | Br | —OCF₂—CHFCl | 99–100 |
| —NHCH₃ | Br | —OCF₂—CHFCl | 191–192 |
| NH₂ | Cl | —OCF₂—CHFCl | 173–174 |
| —NHCH₃ | Cl | —OCF₂—CHFCl | 193–194 |
| NH₂ | Br | —OCF₂—CHFCl | 178–179 |
| —N(CH₃)₂ | Cl | —OCF₂—CHFBr | 85–86 |
| OCH₃ | Cl | —OCF₂—CHFBr | 124–125 |
| —NHCH₃ | Br | —OCF₂—CHFBr | 183–184 |
| —OCH₃ | Br | —OCF₂—CHFBr | 144–145 |
| —N(CH₃)₂ | Br | —OCF₂—CHFBr | 87–88 |
| —NHCH₃ | Cl | —OCF₂—CHFBr | 186–187 |

Application of the herbicide may be effected for instance in the form of directly sprayable solutions, powders, suspensions (including high-percentage, aqueous, oily or other suspensions or dispersions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredients.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compounds such as substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted dihydropyran diones
substituted naphthoquinones
substituted cyclohexane diones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts,
esters and amides substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before planting (with or without incorporation) or after planting, before sowing (with or without incorporation), and before (with or without incorporation), during or after emergence of the crop plants and unwanted plants.

The herbicides according to the invention may be employed in cereal crop such as

| | |
|---|---|
| *Avena* spp. | *Sorghum* |
| *Triticum* spp. | *Zea mays* |
| *Hordeum* spp. | *Panicum miliaceum* |
| *Secale* spp. | *Oryza* spp. |
| *Saccharum offinicarum* | |
| and in *dicotyledon* crops such as | |
| *Cruciferae*, e.g. | spp. |
| *Brassica* spp. | *Raphanus* spp. |
| *Sinapis* spp. | *Lepidium* spp. |
| *Compositae*, e.g. | |
| *Lactuca* spp. | |
| *Helianthus* spp. | *Carthamus* spp. |
| *Malvaceae*, e.g. | *Scorzonera* spp. |
| *Gossypium hirsutum* | |
| *Leguminosae*, e.g. | |
| *Medicago* spp. | *Phaseclus* spp. |
| *Trifolium* spp. | *Arachis* spp. |

-continued

| | |
|---|---|
| *Pisum* spp. | *Glycine* max. |
| *Chenopodiaceae*, e.g. | |
| *Beta vulgaris* | |
| *Spinacia* spp. | |
| *Solanaceae*, e.g. | |
| *Solanum* spp. | *Capsicum annuum* |
| *Nicotiania* spp. | |
| *Linaceae*, e.g. | |
| *Linum* spp. | |
| *Umbelliferae*, e.g. | |
| *Petroselinum* spp. | *Apium graveolens* |
| *Daucus carota* | |
| *Rosaceae*, e.g. | *Fragaria* |
| *Curcurbitaceae*, e.g. | |
| *Cucumis* spp. | *Cucurbita* spp. |
| *Liliaceae*, e.g. | |
| *Allium* spp. | |
| *Vitaceae*, e.g. | |
| *Vitis vinifera* | |
| *Bromeliaceae*, e.g. | |
| *Ananas sativus.* | |

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as

| | |
|---|---|
| *Cynodon* spp. | *Dactylis* spp. |
| *Digitaria* spp. | *Avena* spp. |
| *Echinochloa* spp. | *Bromus* spp. |
| *Setaria* spp. | *Uniola* spp. |
| *Panicum* spp. | *Poa* spp. |
| *Alopecurus* spp. | *Leptochloa* spp. |
| *Lolium* spp. | *Brachiaria* spp. |
| *Sorghum* spp. | *Eleusine* spp. |
| *Agropyron* spp. | *Cenchrus* spp. |
| *Phalaris* spp. | *Eragrostis* spp. |
| *Apera* spp. | *Phragmites communis* |
| etc.; | |
| *Cyperaceae*, such as | |
| *Carex* spp. | *Eleocharis* spp. |
| *Cyperus* spp. | *Scirpus* spp. |
| etc.; | |
| dicotyledonous weeds, such as | |
| *Malvaceae*, e.g., | |
| *Abutilon theoprasti* | *Hibiscus* spp. |
| *Sida* spp. | *Malva* spp. |
| etc.; | |
| *Compositae*, such as | |
| *Ambrosia* spp. | *Centaurea* spp. |
| *Lactuca* spp. | *Tussilago* spp. |
| *Senecio* spp. | *Lapsana communis* |
| *Sonchus* spp. | *Tagetes* spp. |
| *Xanthium* spp. | *Erigeron* spp. |
| *Iva* spp. | *Anthemis* spp. |
| *Galinsoga* spp. | *Matricaria* spp. |
| *Taraxacum* spp. | *Artemisia* spp. |
| *Chrysanthemum* spp. | *Bidens* spp. |
| *Cirsium* spp. | etc.; |
| *Convolvulaceae*, such as | |
| *Convolvulus* spp. | *Cuscuta* spp. |
| *Ipomoea* spp. | *Jaquemontia tamnifolia* |
| etc.; | |
| *Cruciferae*, such as | |
| *Barbarea vulgaris* | *Arabidopsis thaliana* |
| *Brassica* spp. | *Descurainia* spp. |
| *Capsella* spp. | *Draba* spp. |
| *Sisymbrium* spp. | *Coronopus didymus* |
| *Thlaspi*spp. | *Lepidium*spp. |
| *Sinapis arvensis* | *Raphanus* spp. |
| etc.; | |
| *Geraniaceae*, such as | |
| *Erodium* spp. | *Geranium* spp. |
| etc.; | |
| *Portulacaceae*, such as | |
| *Portulaca* spp. | etc.; |
| *Primulaceae*, such as | |
| *Anagallis arvensis* | *Lysimachia* spp. |
| etc.; | |
| *Rubiaceae*, such as | |

-continued

| | |
|---|---|
| Richardia spp. | Diodia spp. |
| Galium spp. | etc.; |
| Scrophulariaceae, such as | |
| Linaria spp. | Digitalis spp. |
| Veronica spp. | etc.; |
| Solanaceae, such as | |
| Physalis spp. | Nicandra spp. |
| Solanum spp. | Datura spp. |
| etc.; | |
| Urticaceae, such as | |
| Urtica spp. | |
| Violaceae, such as | |
| Viola spp. | etc.; |
| Zygophyllaceae, such as | |
| Tribulus terrestris | etc.; |
| Euphorbiaceae, such as | |
| Mercurialis annua | Euphorbia spp. |
| Umbelliferae, such as | |
| Daucus carota | Ammi majus |
| Aethusa cynapium | etc.; |
| Commelinaceae, such as | |
| Commelina spp. | etc.; |
| Labiatae, such as | |
| Lamium spp. | Galeopsis spp. |
| etc.; | |
| Leguminosae, such as | |
| Medicago spp. | Sesbania exaltata |
| Trifolium spp. | Cassia spp. |
| Vicia spp. | Lathyrus spp. |
| etc.; | |
| Plantaginaceae, such as | |
| Plantago spp. | etc.; |
| Polygonaceae, such as | |
| Polygonum spp. | Fagopyrum spp. |
| Rumex spp. | etc.; |
| Aizoaceae, such as | |
| Mollugo verticillata | etc.; |
| Amaranthaceae, such as | |
| Amaranthus spp. | etc.; |
| Boraginaceae, such as | |
| Amsinckia spp. | Anchusa spp. |
| Myostis spp. | Lithospermum spp. |
| etc.; | |
| Caryophyllaceae, such as | |
| Stellaria spp. | Silene spp. |
| Spergula spp. | Cerastium spp. |
| Saponaria spp. | Agrostemma githago |
| Scleranthus annuus | etc.; |
| Chenopodiaceae, such as | |
| Chenopodium spp. | Atriplex spp. |
| Kochia spp. | Monolepsis nuttalliana |
| Salsola Kali | etc.; |
| Lythraceae, such as | |
| Cuphea spp. | etc.; |
| Oxalidaceae, such as | |
| Oxalis spp. | |
| Ranunculaceae, such as | |
| Ranunculus spp. | Adonis spp. |
| Delphinium spp. | etc.; |
| Papaveraceae, such as | |
| Papaver spp. | Fumaria offinicalis |
| etc.; | |
| Onagraceae, such as | |
| Jussiaea spp. | etc.; |
| Rosaceae, such as | |
| Alchemillia spp. | Potentilla spp. |
| etc.; | |
| Potamogetonaceae, such as | |
| Potamogeton spp. | etc.; |
| Najadeceae, such as | |
| Najas spp. | etc.; |
| Equisetaceae | |
| Equisetum spp. | etc.; |
| Marsileaceae, such as | |
| Marsilea quadrifolia | etc.; |
| Polypodiaceae, | |
| Pteridium aquilinum | |
| Alismataceae, such as | |
| Alisma spp. | Sagittaria sagittifolia |
| etc. | |

EXAMPLE 4

In the greenhouse, loamy sandy soil was filled into pots and sown with various seeds. The soil was then immediately treated with active ingredient I and, for comparison purposes, with prior art compound II 1-(m-trifluoromethylphenyl)-4-dimethylamino-5-chloropyridazone-(6), each substance being dispersed or emulsified in 500 liters of water per hectare. The application rate was 1 kg/ha (in the case of the crop plant) and 0.4 kg/ha (in the case of the unwanted plants). During the experiment the soil was kept thoroughly moist. After 4 to 5 weeks it was ascertained that active ingredient I had the same good crop tolerance as II, but a better herbicidal action.

The results are given below:

| Active ingredient kg/ha | I 1 | II 1 |
|---|---|---|
| Crop plant: | | |
| Triticum aestivum | 0 | 0 |
| Active ingredient kg/ha | I 0.4 | II 0.4 |
| Unwanted plants: | | |
| Alopecurus myosuroides | 90 | 80 |
| Echinochloa crus-galli | 90 | 85 |

0 = no damage
100 = complete destruction

EXAMPLE 5

In the greenhouse, various plants were treated at a growth height of from 7 to 12 cm with active ingredient I and, for comparison, compound II, each substance being emulsified or dispersed in 500 liters of water per hectare. After 2 to 3 weeks it was ascertained that active ingredient I at 0.5 kg/ha had better crop tolerance than II, and at 0.4 kg/ha a stronger herbicidal action than II.

The results are given below:

| Active ingredient kg/ha | I 0.5 | II 0.5 |
|---|---|---|
| Crop plant: | | |
| Gossypium hirsutum | 10 | 30 |
| Active ingredient kg/ha | I 0.4 | II 0.4 |
| Unwanted plant: | | |
| Echinochloa crus-galli | 80 | 60 |

0 = no damage
100 = complete destruction

EXAMPLE 6

An agricultural plot was sown with various seeds. The plot was then immediately treated with 3 kg/ha of each of active ingredients I, III and IV, each being dispersed or emulsified in 500 liters of water per hectare.

After 4 to 5 weeks it was ascertained that active ingredients I, III and IV had a strong herbicidal action and were well tolerated by the crop plant.

The results are given below:

| Active ingredient kg/ha | I 3 | III 3 | IV 3 |
|---|---|---|---|
| Crop plant: | | | |
| Gossypium hirsutum | 10 | 10 | 10 |
| Unwanted plants: | | | |
| Amaranthus retroflexus | 100 | 100 | 100 |
| Chenopodium album | 85 | 100 | 95 |
| Matricaria chamomilla | 100 | 100 | 100 |
| Sinapis arvensis | 90 | 100 | 100 |
| Stellaria media | 80 | 100 | 90 |
| Thlaspi arvense | 100 | 100 | 100 |
| Galium aparine | — | 90 | 90 |
| Alopecurus myosuroides | — | 90 | 90 |
| Echinochloa crus-galli | — | 90 | 90 |

0 = no damage
100 = complete destruction

EXAMPLE 7

90 parts by weight of compound I is mixed with 10 parts by weight of N-methyl-χ-pyrrolidone. A mixture is obtained which is suitable for application in the form of very fine drops.

EXAMPLE 8

20 parts by weight of compound III is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound IV is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound III is well mixed with 3 parts by weight of the sodium salt of diisobutylnaphthalene-χ-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound IV is intimately mixed with 97 parts by weight of particulate kaolin. A dust is obtained containing 3% by weight of the active ingredient.

EXAMPLE 13

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

In the greenhouse, loamy sandy soil was filled into pots and sown with the seeds of various test plants, separated by species. The soil was then immediately treated with the following active ingredients, each being dispersed or emulsified in 500 liters of water per hectare. The application rates were 0.25, 0.5, 1.0 and 2.0 kg/ha. During the experiment the soil in the pots was kept thoroughly moist.

| Active ingredient | $R^1$ | $R^2$ | $R^3$ |
|---|---|---|---|
| I | $-N(CH_3)_2$ | Cl | $-OCF_2-CHF_2$ |
| III | $-OCH_3$ | Cl | $-OCF_2-CHF_2$ |
| IV | $-NH(CH_3)$ | Cl | $-OCF_2-CHF_2$ |
| V | $-OCH_3$ | Cl | $-CF_3$ (prior art) |
| VI | $-NH(CH_3)$ | Cl | $CF_3$ (prior art) |
| VII | $-NH_2$ | Cl | H (prior art) |
| VIII | $-NH_2$ | Br | H (prior art) |

The action of the compounds on the various test plants after 4 to 5 weeks is apparent from the following table:

| Test plants | Application rate kg/ha | I | III | IV | V | VI | VII | VIII |
|---|---|---|---|---|---|---|---|---|
| Gossypium hirsutum | 0.25 | 10 | 0 | 20 | 10 | 30 | — | — |
|  | 0.5 | 10 | 0 | 20 | 10 | 30 | 30 | 70 |
|  | 1.0 | 15 | 0 | 20 | 20 | 30 | 80 | 70 |
|  | 2.0 | 20 | 0 | 20 | 20 | 80 | 95 | 90 |
| Echinochloa crus-galli | 0.25 | 100 | 20 | 95 | 50 | 95 | — | — |
|  | 0.5 | 100 | 90 | 100 | 90 | 95 | 50 | 50 |
|  | 1.0 | 100 | 100 | 100 | 95 | 95 | 60 | 80 |
|  | 2.0 | — | — | — | — | — | 85 | 95 |
| Eleusine indica | 0.25 | 80 | 60 | 90 | 30 | 95 | — | — |
|  | 0.5 | 100 | 85 | 95 | 80 | 95 | — | — |
|  | 1.0 | 100 | 85 | 100 | 85 | 100 | — | — |
|  | 2.0 | — | — | — | — | — | — | — |
| Setaria | 0.25 | 100 | 90 | 100 | 80 | 100 | — | — |

-continued

| Test plants | Application rate kg/ha | Active ingredient and assessment | | | | | | |
|---|---|---|---|---|---|---|---|---|
| | | I | III | IV | V | VI | VII | VIII |
| faberii | 0.5 | 100 | 95 | 100 | 100 | 100 | 90 | 95 |
| | 1.0 | 100 | 100 | 100 | 100 | 100 | 90 | 95 |
| | 2.0 | — | — | — | — | — | 95 | 100 |
| Cyperus esculentus | 0.25 | 40 | 10 | 50 | 30 | 60 | — | — |
| | 0.5 | 70 | 20 | 65 | 50 | 100 | — | — |
| | 1.0 | 90 | 50 | 70 | — | 100 | — | — |
| | 2.0 | — | — | — | — | — | — | — |
| Ipomoea lacunosa | 0.25 | 55 | 30 | 50 | 30 | 60 | — | — |
| | 0.5 | 80 | 40 | 75 | 30 | 75 | — | — |
| | 1.0 | 85 | 50 | 95 | 40 | 85 | — | — |
| | 2.0 | — | — | — | — | — | — | — |
| Sida spinosa | 0.25 | 90 | 30 | 50 | 30 | 60 | — | — |
| | 0.5 | 95 | 40 | 75 | 30 | 75 | — | — |
| | 1.0 | 95 | 50 | 95 | 40 | 85 | — | — |
| | 2.0 | — | — | — | — | — | — | — |

These results may be summarized as follows.

Cotton clearly tolerates I, III and IV better than VI.

The action of I and IV on unwanted grasses is very good.

The action of I and IV on broadleaved unwanted species is the same as, or better than, that of VI.

Active ingredient V takes up an intermediate position with regard to compatibility in cotton. The action on unwanted plants was inferior to that of I and IV. The action of III on unwanted plants was similar to that of V, but its compatibility with cotton was excellent and better than that of V.

The action of the following compounds corresponds to that of I, III and IV:

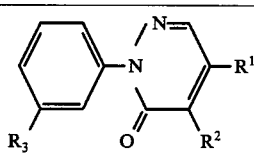

| $R^1$ | $R^2$ | $R^3$ |
|---|---|---|
| $-N\overset{H}{\underset{C-CH_2Cl}{\diagdown}}$ (C=O) | Cl | $-OCF_2-CHF_2$ |
| $-N\overset{H}{\underset{C-CH_2-O-C-CH_3}{\diagdown}}$ (C=O, C=O) | Cl | $-OCF_2-CHF_2$ |
| $-N\diagup\diagdown$ (azetidinyl) | Cl | $-OCF_2-CHF_2$ |
| $-NH_2$ | Cl | $-OCHF_2$ |
| $-NH(CH_3)$ | Cl | $-OCHF_2$ |
| $-N(CH_3)_2$ | Cl | $-OCHF_2$ |

-continued

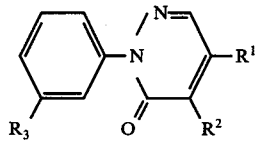

| $R^1$ | $R^2$ | $R^3$ |
|---|---|---|
| $-N\overset{H}{\underset{C-CH_2Cl}{\diagdown}}$ | Cl | $-OCHF_2$ |
| $-N\overset{H}{\underset{C-CH_2-O-C-CH_3}{\diagdown}}$ | Cl | $-OCHF_2$ |
| $-OCH_3$ | Cl | $-OCHF_2$ |
| $-NH_2$ | Cl | $-OCF_2CHF_2$ |
| $-NH_2$ | Br | $-OCF_2CHF_2$ |

EXAMPLE 15

Loamy sandy soil was filled into paraffined paper beakers having a volume of 170 cm³; the following test plants, separated by species, were sown shallow:

Latin name

Cyperus esculentus
Echinochloa crus galli
Eleusine indica
Euphorbia geniculata
Gossypium hirsutum
Ipomoea spp. usually I. lacunosa
Setaria faberii
Sida spinosa The compounds were applied preemergence immediately after sowing. The seeds had not yet germinated; only the tubers of Cyperus esculentus had tips showing. The agents were suspended or emulsified in water as diluent and sprayed through atomizing nozzles. The soil was watered regularly during the experiment. The beakers were kept in the warm part of the greenhouse (18° to 26° C). The observation period was 4 weeks. Assessment was visual, employing a 0 to 100 scale on which 0 = no damage and 100 = complete destruction. The germinating cotton plants were also thinned out to 5 per vessel; the dry substance was determined herefrom after completion of the experiment.

Results (1) The excellent herbicidal action of the new compounds 1-(m-tetrafluoroethoxyphenyl)-4-dimethylamino-5-chloropyridazone-6 (I) and 1-(m-tetrafluoroethoxyphenyl)-4-methylamino-5-chloropyridazone-6 (IV) was as good as that of analogous prior art compounds (Table 1).

(2) Of decisive importance is the superior tolerance in the crop plant cotton, which is particularly in evidence in a comparison of IV with VI, the prior art compound coming chemically closest to it (Table 1).

(a) Even at very high application rates the plants treated with IV yielded dry substance amounts which differed insignificantly from those of the untreated plants; by contrast, the two high application rates in the case of compound VI caused a significant drop in the amount of dry substance compared with the untreated plants.

(b) In a direct comparison of the two compounds IV and VI, no differences can be detected with any certainty at an application rate of 2.0 kg/ha, but there are indications that compound IV is better tolerated. The plants treated with IV at the highest application rate of 4.0 kg/ha showed however significantly improved growth, which thus proves the superior compatibility of this new substance with cotton.

(3) Some of the other new compounds of the same class had a similar, and sometimes a somewhat weaker, action on unwanted plants. The selectivity of 1-(m-difluoromethoxyphenyl)-4-dimethylamino-5-bromopyridazone-(6) (XI) in cotton was however excellent and far better than that of the comparative agents (Table 2).

Table 1 - Legend

+) 0 = no damage
100 = complete destruction

++) Duncan's new multiple range test, level 0.05%; values which have any letter(s) in common are not significantly different.

Table 1

Weed control and tolerance in cotton (*Gossypium hirsutum*) of new m-phenyl substituted pyridazones Basic molecule

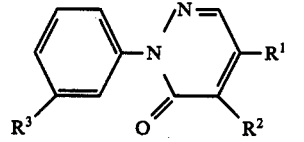

| Active ingredients and substituents R¹ | R² | R³ | Application rate kg/ha | % damage to unwanted plants+) |  |  |  |  | Dry substance of young cotton plants in g/vessel |
|---|---|---|---|---|---|---|---|---|---|
|  |  |  |  | Echinochloa crus galli | Euphorbia geniculata | Ipomoea spp. | Setaria faberii | Sida spinosa |  |
| Control | — | — | — | 0 | 0 | 0 | 0 | 0 | 1.15 ab++) |
| VII—N⟨H,H | Cl | H (prior art) | 0.5 | 40 | 22.5 | 35 | 55 | 90 | 0.70 de |
|  |  |  | 1.0 | 72.5 | 50 | 40 | 95 | 90 | 0.69 de |
|  |  |  | 2.0 | 90 | 87.5 | 87.5 | 95 | 95 | 0.43 ef |
|  |  |  | 4.0 | 92.5 | 95 | 95 | 95 | 95 | 0.20 f |
| II—N⟨CH₃,CH₃ | Cl | —CF₃ (prior art) | 0.5 | 95 | 95 | 90 | 95 | 95 | 1.07 abc |
|  |  |  | 1.0 | 95 | 95 | 95 | 95 | 95 | 0.97 abcd |
|  |  |  | 2.0 | 95 | 95 | 95 | 95 | 95 | 1.08 abc |
|  |  |  | 4.0 | 95 | 95 | 95 | 95 | 95 | 0.82 cd |
| VI—N⟨H,CH₃ | Cl | —CF₃ (prior art) | 0.5 | 95 | 95 | 87.5 | 95 | 95 | 0.97 abcd |
|  |  |  | 1.0 | 95 | 95 | 92.5 | 95 | 95 | 1.23 a |
|  |  |  | 2.0 | 95 | 95 | 92.5 | 95 | 95 | 0.70 de |
|  |  |  | 4.0 | 95 | 95 | 95 | 95 | 95 | 0.52 e |
| I—N⟨CH₃,CH₃ | Cl | —OCF₂—CHF₂ | 0.5 | 95 | 85 | 92.5 | 95 | 95 | 0.95 abcd |
|  |  |  | 1.0 | 95 | 85 | 95 | 95 | 95 | 0.85 bcd |
|  |  |  | 2.0 | 95 | 92.5 | 95 | 95 | 95 | 0.97 abcd |
|  |  |  | 4.0 | 95 | 95 | 95 | 95 | 95 | 0.91 abcd |
| IV—N⟨H,CH₃ | Cl | —OCF₂—CHF₂ | 0.5 | 95 | 95 | 92.5 | 95 | 95 | 1.12 ab |
|  |  |  | 1.0 | 95 | 95 | 95 | 95 | 95 | 1.03 abc |
|  |  |  | 2.0 | 95 | 95 | 95 | 95 | 95 | 0.97 abcd |
|  |  |  | 4.0 | 95 | 95 | 95 | 95 | 95 | 0.91 abcd |

Table 2

Weed control and tolerance in cotton (*Gossypium hirsutum*) of other new m-phenyl substituted pyridazones Basic molecule

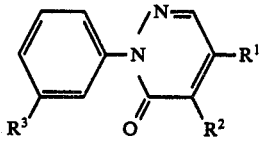

| Active ingredients and substituents R¹ | R² | R³ | Application rate kg/ha | Test plants and % damage |  |  |  |  |  |
|---|---|---|---|---|---|---|---|---|---|
|  |  |  |  | Gossypium hirsutum | Cyperus esculentus | Echinochloa crus galli | Eleusine indica | Euphorbia geniculata | Setaria faberii | Sida spinosa |
| IX OCH₃ (prior art) | Cl | CF₃ | 0.5 | 10 | 40 | 68.3 | 70 | 20 | 100 | 85 |
|  |  |  | 2.0 | 40 | — | 97.7 | — | 95 | 100 | 97.5 |
|  |  |  | 4.0 | — | — | 95.0 | — | — | — | — |

Table 2-continued
Weed control and tolerance in cotton (*Gossypium hirsutum*) of other new m-phenyl substituted pyridazones Basic molecule

| Active ingredients and substituents | | | Application rate kg/ha | Test plants and % damage | | | | | | |
|---|---|---|---|---|---|---|---|---|---|---|
| R¹ | R² | R³ | | *Gossypium hirsutum* | *Cyperus esculentus* | *Echinochloa crus galli* | *Eleusine indica* | *Euphorbia geniculata* | *Setaria faberii* | *Sida spinosa* |
| II —N(CH₃)(CH₃) (prior art) | Cl | CF₃ | 0.5 | 17 | 30 | 93.8 | 96.7 | 92.5 | 95 | 97 |
| | | | 2.0 | 32 | 62.5 | 97 | 95 | 100 | 95 | 97 |
| | | | 4.0 | 37.5 | 68 | 95 | 95 | — | 95 | 95 |
| X OCH₃ | Br | —OCHF₂ | 0.5 | 10 | 30 | 20 | 25 | 30 | — | 95 |
| | | | 2.0 | 10 | 50 | 80 | 90 | 95 | 95 | 95 |
| | | | 4.0 | 30 | — | 92.5 | 95 | — | 95 | 95 |
| XI —N(CH₃)(CH₃) | Br | —OCHF₂ | 0.5 | 0 | — | 40 | 80 | 90 | 60 | 90 |
| | | | 2.0 | 0 | — | 90 | 95 | 95 | 95 | 95 |
| | | | 4.0 | 0 | — | 90 | 95 | — | 95 | — |
| XII OCH₃ | Cl | OCHF₂ | 0.5 | 0 | 0 | 50 | — | 25 | 55 | 90 |
| | | | 2.0 | 5 | 0 | 95 | — | 45 | 100 | 100 |
| | | | 4.0 | 30 | 0 | — | — | — | — | — |
| XIII —N(CH₃)(CH₃) | Cl | —OCHF₂ | 0.5 | 5 | 10 | 50 | — | 85 | 100 | 80 |
| | | | 2.0 | 40 | 10 | 100 | — | 100 | 100 | 100 |
| | | | 4.0 | 40 | 10 | 10 | — | — | — | — |

0 = no damage
100 = complete destruction

EXAMPLE 16

Different crops call for varying periods of action of weedicides. For instance, in crops having a short vegetation period (e.g. vegetables) the agents employed should have short persistence, whereas in permanent crops (e.g. small fruit, grapes, hops) herbicides having long persistence are desirable. Even greater persistence is required of agents for removing unwanted plants from paths and ways, squares and playgrounds and the like, railroad track, industrial plants, etc. The persistence of the new compounds in the soil was investigated by means of a biotest.

Loamy sandy soil containing 1.5% humus was filled into paper beakers having a volume of 170 cm³; the surface of the soil was treated with the active ingredients and at the application rates given in Table 3. The agents was applied using water as diluent and through atomizing spray nozzles. The vessels were kept at a temperature of from 15° to 30° C for the duration of the experiment and cared for in accordance with the horticultural art. During the first two months following the application of the active ingredients the soil was regularly watered, the germinating plants were removed and the surface of the soil was broken up. The test plants employed to demonstrate persistence were *Sinapis alba* (white mustard) and *Sorghum bicolor* (milo grain corghum, Funk's hybrid variety). Both were sown separately after two months, and their growth was observed for 4 to 6 weeks. The damage was assessed visually on a 0 to 100 scale (0 = no influence on growth, 100 = plants destroyed).

The results are given in Table 3. The new compounds I and IV demonstrated considerable persistence in the soil.

There is thus justification in using these compounds not only in some agricultural crops, but also for the uses mentioned above, where greater persistence is desirable.

Table 3
Persistence of new m-phenyl substituted pyridazones

Basic molecule 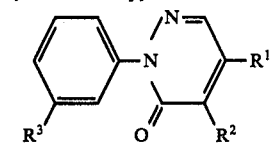

| Active ingredients and substituents | | | Application rate | Test plants and % damage; seeds sown two months after treatment of the soil | |
|---|---|---|---|---|---|
| R¹ | R² | R³ | kg/ha | *Sinapis alba* | *Sorghum bicolor* |
| VII —N(H)(H) | Cl (prior art) | H | 0.25 | 10 | — |
| | | | 0.5 | 15 | 10 |
| | | | 1.0 | 25 | 20 |
| | | | 2.0 | 30 | 30 |
| | | | 4.0 | — | 38 |

Table 3-continued

Persistence of new m-phenyl substituted pyridazones

Basic molecule 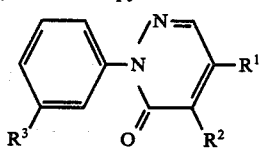

| Active ingredients and substituents R¹ | R² | R³ | Application rate kg/ha | Test plants and % damage; seeds sown two months after treatment of the soil | |
|---|---|---|---|---|---|
| | | | | Sinapis alba | Sorghum bicolor |
| II  −N(CH₃)(CH₃) | Cl | −CF₃ (prior art) | 0.25 | 30 | — |
| | | | 0.5 | 45 | 25 |
| | | | 1.0 | 95 | 45 |
| | | | 2.0 | 98 | 90 |
| | | | 4.0 | — | 95 |
| VI  −N(H)(CH₃) | Cl | −CF₃ (prior art) | 0.25 | 78 | — |
| | | | 0.5 | 85 | 72 |
| | | | 1.0 | 98 | 92 |
| | | | 2.0 | 98 | 98 |
| | | | 4.0 | — | 98 |
| I  −N(CH₃)(CH₃) | Cl | −OCF₂−CHF₂ | 0.25 | 32 | — |
| | | | 0.5 | 42 | 48 |
| | | | 1.0 | 75 | 95 |
| | | | 2.0 | 95 | 95 |
| | | | 4.0 | — | 98 |
| IV  −N(H)(CH₃) | Cl | −OCF₂−CHF₂ | 0.25 | 68 | — |
| | | | 0.5 | 98 | 75 |
| | | | 1.0 | 98 | 82 |
| | | | 2.0 | 98 | 88 |
| | | | 4.0 | — | 98 |

0 = no damage
100 = complete destruction

EXAMPLE 17

Postemergence action of m-phenyl substituted pyridazones

The herbicidal action of m-phenyl substituted pyridazone derivatives when applied prior to emergence of the unwanted plants has already been illustrated in the foregoing examples. In further experiments the effect of new compounds of this class when applied to the plant during growth (leaf treatment, postemergence treatment) was investigated. The test plants, separated by species, were grown from seed to a height of 3 to 10 cm in vessels (paraffined paper cups having a volume of 170 cm³) filled with loamy sandy oil. The plants were then treated with the active ingredients in the table below at the application rates mentioned therein. They were emulsified or suspended in water as carrier and sprayed onto the plants through atomizing nozzles. For the 4-week duration of the experiment the vessels were kept thoroughly moist in the greenhouse. The scale employed in the visual assessment was 0 to 100 (0 = no damage, 100 = complete destruction).

When applied postemergence the new compounds exhibited an exceptional action on unwanted plants. Their effects are similar when applied to the soil pre-emergence. They therefore offer the special advantage of a - for herbicides - very wide scope with regard to the time of application because of their leaf and residual action. In the case of herbaceous crop plants which are sensitive to these compounds when they are applied to the leaf, technical measures may be adopted in order to prevent direct contact of the spray liquor with the leaves (e.g. post-directed spray or layby treatment).

| List of test plants: | |
|---|---|
| Latin name | Abbreviation in tables |
| Alopecurus myosuroides | Alopec. myosur. |
| Avena fatua | Avena fatua |
| Cyperus esculentus | Cyperus escul. |
| Cynodon dactylon | Cynodon dactl. |
| Echinochloa crus galli | Echinochloa c.g. |
| Ipomoea spp. | Ipomoea spp. |
| Sorghum halepense | Sorghum hal. |

Table 4

Weed Control afforded by some m-phenyl subtituted pyridazone derivatives when applied postemergence (leaf treatment)

Basic molecule

| | Active ingredients and substituents | | | Application rates kg/ha | Test plants and % damage | | | | | | |
|---|---|---|---|---|---|---|---|---|---|---|---|
| | $R^1$ | $R^2$ | $R^3$ | | Alopec. myosur. | Avena fatua | Cyperus escul. | Cynodon dactl. | Echinochloa c.g. | Ipomoea spp. | Sorghum hal. |
| IX | —OCH$_3$ (prior art) | Cl | CF$_3$ | 1.0 | 90 | 80 | 95 | 50 | 90 | 40 | 90 |
| | | | | 2.0 | 90 | 90 | 95 | 50 | 90 | 60 | 90 |
| | | | | 4.0 | 90 | 90 | — | — | — | — | — |
| II | —N(CH$_3$)(CH$_3$) (prior art) | Cl | CF$_3$ | 1.0 | 80 | 30 | 95 | 30 | 100 | 40 | 80 |
| | | | | 2.0 | 90 | 65 | 95 | 30 | 100 | 40 | 80 |
| | | | | 4.0 | 90 | 70 | — | — | 100 | — | — |
| VI | —N(H)(CH$_3$) (prior art) | Cl | —CF$_3$ | 1.0 | 100 | 85 | 95 | 70 | 100 | 45 | 85 |
| | | | | 2.0 | 100 | 85 | 95 | 70 | 100 | 45 | 85 |
| | | | | 4.0 | 100 | 85 | — | — | 100 | — | — |
| IV | —N(H)(CH$_3$) | Cl | —OCF$_2$—CHF$_2$ | 1.0 | 90 | 87 | 100 | — | 98 | — | 100 |
| | | | | 2.0 | 98 | 95 | 100 | — | 98 | — | 100 |
| | | | | 4.0 | — | — | — | — | — | — | — |
| XIV | —N(H)(CH$_3$) | Br | —OCF$_3$ | 1.0 | 100 | 80 | — | — | 100 | — | — |
| | | | | 2.0 | 100 | 90 | — | — | 100 | — | — |
| | | | | 4.0 | 100 | 90 | — | — | 100 | — | — |
| XV | —N(H)(CH$_3$) | Cl | —OCF$_3$ | 1.0 | 80 | 70 | — | — | 98 | — | — |
| | | | | 2.0 | 80 | 80 | — | — | 98 | — | — |
| | | | | 4.0 | 100 | 80 | — | — | 98 | — | — |
| XVI | —N(H)(H) | Br | —OCF$_3$ | 1.0 | 70 | 95 | — | — | 100 | — | — |
| | | | | 2.0 | 80 | 98 | — | — | 100 | — | — |
| | | | | 4.0 | 80 | — | — | — | 100 | — | — |
| XVII | OCH$_3$ | Cl | —OCF$_2$—CHBrF | 1.0 | 98 | 80 | 95 | 90 | 80 | 35 | 90 |
| | | | | 2.0 | 98 | 80 | 95 | 90 | 90 | 80 | 90 |
| | | | | 4.0 | 98 | 100 | — | — | — | — | — |
| XVIII | —N(H)(CH$_3$) | Br | —OCHF$_2$ | 1.0 | 98 | 0 | 90 | 90 | 95 | 10 | 90 |
| | | | | 2.0 | 98 | 0 | 95 | 90 | 95 | 70 | 95 |
| | | | | 4.0 | 98 | 20 | — | — | — | — | — |
| XIX | —N(CH$_3$)(CH$_3$) | Cl | —OCF$_2$—CHBrF | 1.0 | 98 | 70 | 95 | 90 | 80 | 50 | 90 |
| | | | | 2.0 | 100 | 80 | 95 | 90 | 80 | 60 | 90 |
| | | | | 4.0 | 100 | 80 | — | — | — | — | — |
| XX | —OCH$_3$ | Cl | —OCF$_3$ | 1.0 | 100 | 98 | 95 | 70 | 95 | 20 | 60 |
| | | | | 2.0 | 100 | 98 | 95 | 80 | 95 | 45 | 90 |
| | | | | 4.0 | 100 | 98 | — | — | — | — | — |
| XXI | —N(CH$_3$)(CH$_3$) | Cl | —OCF$_3$ | 1.0 | 90 | 60 | — | — | 90 | — | — |
| | | | | 2.0 | 90 | 60 | — | — | 100 | — | — |
| | | | | 4.0 | 90 | 80 | — | — | 100 | — | — |
| XXII | —N(CH$_3$)(CH$_3$) | Cl | —OCF$_2$—CHClF | 1.0 | 80 | 80 | — | — | 85 | — | — |
| | | | | 2.0 | 90 | 80 | — | — | 90 | — | — |
| | | | | 4.0 | 90 | 80 | — | — | 90 | — | — |
| XXIII | —N(CH$_3$)(CH$_3$) | Br | OCF$_2$—CHClF | 1.0 | 90 | 70 | — | — | 90 | — | — |
| | | | | 2.0 | 90 | 80 | — | — | 100 | — | — |
| | | | | 4.0 | 90 | 80 | — | — | 100 | — | — |
| XXIV | —N(H)(CH$_3$) | Cl | OCHF$_2$ | 1.0 | 100 | 90 | — | — | 90 | — | — |
| | | | | 2.0 | 100 | 100 | — | — | 100 | — | — |
| | | | | 4.0 | 100 | 100 | — | — | 100 | — | — |

0 = no damage
100 = complete destruction

We claim:

1. A substituted pyridazone selected from the group consisting of 1-(m-tetrafluoroethoxyphenyl)-4-amino-5-chloropyridazone-6, 1-(m-tetrafluoroethoxyphenyl)-4-amino-5-bromopyridazone-6, 1-(m-tetrafluoroethoxyphenyl)-4-methylamino-5-chloropyridazone-6, 1-(m-tetrafluoroethoxyphenyl)-4-methylamino-5-bromopyridazone-6, 1-(m-tetrafluoroethoxyphenyl)-4-dimethylamino-5-chloropyridazone-6, 1-(m-tetrafluoroethoxyphenyl)-4-dimethylamino-5-bromopyridazone-6, 1-(m-tetrafluoroethoxyphenyl)-4-methoxy-5-chloropyridazone-6 and 1-(m-tetrafluoroethoxyphenyl)-4-methoxy-5-bromopyridazone-6.

2. A substituted pyridazone as claimed in claim 1 wherein the compound has the formula

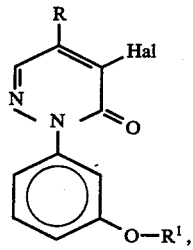

wherein Hal is chloro, $R^1$ is tetrafluoroethyl and R is methylamino or dimethylamino.

3. A substituted pyridazone as claimed in claim 1 wherein the compound has the formula

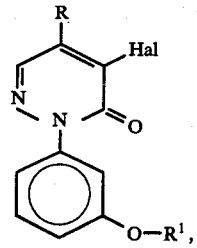

wherein Hal is chloro, $R^1$ is tetrafluoroethyl and R is methoxy.

4. A substituted pyridazone of the formula

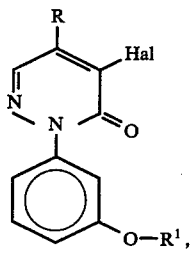

wherein Hal is bromo or chloro, $R^1$ is difluoromethyl and R is methoxy, dimethylamino or methylamino.

5. A process for controlling the growth of unwanted plants among cotton plants wherein the locus of the plants is treated with a phytotoxic amount of a substituted pyridazone selected from the group consisting of 1-(m-tetrafluoroethoxyphenyl)-4-amino-5-chloropyridazone-6, 1-(m-tetrafluoroethoxyphenyl)-4-amino-5-bromopyridazone-6, 1-(m-tetrafluoroethoxyphenyl)-4-methylamino-5-chloropyridaone-6, 1-(m-tetrafluoroethoxyphenyl)-4-methylamino-5-bromopyridaone-6, 1-(m-tetrafluoroethoxyphenyl)-4-dimethylamino-5-chloropyridazone-6, 1-(m-tetrafluoroethoxyphenyl)-4-dimethylamino-5-bromopyridazone-6, 1-(m-tetrafluoroethoxyphenyl)-4-methoxy-5-chloropyridazone-6 and 1-(m-tetrafluoroethoxyphenyl)-4-methoxy-5-bromopyridazone-6.

* * * * *

UNITED STATES PATENT AND TRADEMARK OFFICE
CERTIFICATE OF CORRECTION

PATENT NO. : 4,077,797
DATED : March 7, 1978
INVENTOR(S) : ADOLF FISCHER et al

It is certified that error appears in the above-identified patent and that said Letters Patent are hereby corrected as shown below:

Col. 24, line 38,

"chloropyridaone-6" should read -- chloropyridazone-6 --

Col. 24, line 40,

"bromopyridaone-6" should read -- bromopyridazone-6 --.

Signed and Sealed this

Nineteenth Day of December 1978

[SEAL]

Attest:

RUTH C. MASON
Attesting Officer

DONALD W. BANNER
Commissioner of Patents and Trademarks